United States Patent
Vigot et al.

(10) Patent No.: US 11,738,151 B2
(45) Date of Patent: Aug. 29, 2023

(54) NEEDLELESS INJECTION DEVICE WITH A CURVED MEMBRANE

(71) Applicant: CROSSJECT, Dijon (FR)

(72) Inventors: Xavier Vigot, Veronnes (FR); Christophe Auriel, Binges (FR)

(73) Assignee: CROSSJECT, Dijon (FR)

( * ) Notice: Subject to any disclaimer, the term of this patent is extended or adjusted under 35 U.S.C. 154(b) by 885 days.

(21) Appl. No.: 16/103,514

(22) Filed: Aug. 14, 2018

(65) Prior Publication Data
US 2018/0369486 A1   Dec. 27, 2018

Related U.S. Application Data

(63) Continuation of application No. PCT/FR2017/050323, filed on Feb. 13, 2017.

(30) Foreign Application Priority Data

Feb. 18, 2016 (FR) ...................... 16/51338

(51) Int. Cl.
*A61M 5/30* (2006.01)
*A61M 5/20* (2006.01)
(Continued)

(52) U.S. Cl.
CPC ............ *A61M 5/30* (2013.01); *A61M 5/2046* (2013.01); *A61M 5/2053* (2013.01); *A61M 5/282* (2013.01); *A61M 5/31513* (2013.01)

(58) Field of Classification Search
CPC .... A61M 5/2046; A61M 5/3007; A61M 5/30; A61M 5/2053; A61M 5/282;
(Continued)

(56) References Cited

U.S. PATENT DOCUMENTS

| 3,802,430 A | * | 4/1974 | Schwebel | ............... A61M 5/30 604/69 |
| 6,258,062 B1 | * | 7/2001 | Thielen | ................... A61M 5/30 604/141 |

(Continued)

FOREIGN PATENT DOCUMENTS

| EP | 2366418 | 9/2011 |
| FR | 2815544 | 4/2002 |

(Continued)

OTHER PUBLICATIONS

International Search Report for international application PCT/FR2017/050323, dated May 26, 2017.

*Primary Examiner* — Kami A Bosworth
*Assistant Examiner* — Antarius S Daniel
(74) *Attorney, Agent, or Firm* — Burris Law, PLLC

(57) ABSTRACT

A needleless injection device is provided that includes a body forming a housing, a gas generator, a tubular reservoir that contains an active ingredient, and a T-shaped elastically deformable membrane having a tubular portion. The reservoir extends axially in the housing from an upper end to a lower end and the tubular portion is configured to extend and lie axially in the reservoir under an effect of a pressure generated by the gas generator. An injection nozzle is arranged at the lower end of the reservoir. The tubular portion is funnel shaped and includes at least an upper segment that decreases along an axial elongation direction of the member and a lower segment that increases along the axial elongation direction. The axial length of the upper segment is greater than that of the lower segment.

8 Claims, 2 Drawing Sheets

(51) Int. Cl.
*A61M 5/28* (2006.01)
*A61M 5/315* (2006.01)

(58) Field of Classification Search
CPC ............ A61M 5/31513; A61M 5/1452; A61M 5/14526; A61M 5/315; A61M 5/14586; A61M 5/14593; A61M 2005/31516
See application file for complete search history.

(56) References Cited

U.S. PATENT DOCUMENTS

| | | | |
|---|---|---|---|
| 2003/0114789 A1 | 6/2003 | Haar et al. | |
| 2004/0015125 A1* | 1/2004 | Alexandre | A61M 5/30 604/69 |
| 2007/0055214 A1* | 3/2007 | Gilbert | A61M 5/30 604/500 |
| 2015/0231334 A1* | 8/2015 | Buchine | A61M 5/2448 514/11.7 |
| 2016/0250388 A1* | 9/2016 | Wang | A61K 31/337 604/103.02 |

FOREIGN PATENT DOCUMENTS

| | | |
|---|---|---|
| FR | 2852517 | 9/2004 |
| JP | H08164205 | 6/1996 |

* cited by examiner

NEEDLELESS INJECTION DEVICE WITH A CURVED MEMBRANE

CROSS-REFERENCE TO RELATED APPLICATIONS

This application is a continuation of International Application No. PCT/FR2017/050323, filed on Feb. 13, 2017, which claims priority to and the benefit of FR 16/51338, filed on Feb. 18, 2016. The disclosures of the above applications are incorporated herein by reference.

FIELD

The present disclosure relates to a needleless injection device.

BACKGROUND

The statements in this section merely provide background information related to the present disclosure and may not constitute prior art.

The technical field of the present disclosure is one of the needleless, pre-filled and disposable injection devices, operating with an energy source such as for example a gas generator, and used for the intradermal, subcutaneous and intramuscular injections of liquid active ingredient for therapeutic use in human or veterinary medicine.

The active ingredient is constituted by a more or less viscous liquid, a mixture of liquid, or a gel. The active ingredient may also be a solid dissolved in a solvent suitable for the injection or be constituted of a powdery solid suspended at a certain concentration in a suitable liquid. The particle size of the active ingredient must then be compatible with the diameter of the ducts in order to avoid sealing them.

An injection device includes, in a known manner, as for example in the patent application FR-A-2815544 (equivalent to WO 02/34317), a body comprising successively a gas generator, an expansion chamber, a reservoir containing the liquid active ingredient and an injection system.

The reservoir is constituted by a glass tube which is inserted into a tubular housing delimited by the body of the device, the tube being sealed by an upper or upstream piston and a lower or downstream piston between which the liquid active ingredient is contained.

The lower free end of the reservoir cooperates with an injection nozzle which delimits at least one injection channel extending axially along an injection axis.

The injection nozzle is delimited axially by an upper face axially bearing on the reservoir, and a lower injection face adapted to cooperate with a closure cap.

Furthermore, the injection device includes a hollow cover which wraps the body and which delimits a lower opening adapted for the passage of the injection nozzle.

In order to allow the injection of the active ingredient, the body is slidably mounted in the cover, from bottom to top along a sliding axis, between a rest position and an injection position, the driving of the body being carried out when the user presses the injection nozzle on his skin.

The displacement of the body in the cover allows the triggering of the gas generator, generating a pressurized gas which drives the pistons in displacement to inject the active ingredient through the skin of the patient, by passing through the injection nozzle.

There is known an injection device which is equipped with a generally T-shaped elastically deformable membrane, which comprises a radial annular disc which is axially interposed between the upper end of the reservoir and a seat formed by the body, and a tubular portion which extends axially in the reservoir, from the annular disc.

The tubular portion of the membrane is designed to extend axially under the effect of the pressurized gas, in order to drive the pistons in displacement.

The pressure of the gas also deforms the membrane radially, such that the membrane engages on the inner wall of the glass reservoir.

The friction between the membrane, which is generally made of elastomer, and the glass wall of the reservoir, is significant and absorbs a significant portion of the energy required for the elongation and extension of the tubular portion of the membrane in the reservoir.

In order to overcome this issue, it is known to lubricate the membrane in order to limit the friction between the membrane and the reservoir.

Although effective, the lubrication is a restrictive step during the production and assembly of the injection device.

SUMMARY

The present disclosure relates to a needleless injection device including:
a body forming a housing;
a gas generator;
a tubular reservoir which contains an active ingredient to be injected, the reservoir extending axially in said housing from an upper end, to a lower end;
a generally T-shaped elastically deformable membrane, the membrane comprising a tubular portion which extends axially in the reservoir and which is designed to lie axially in the reservoir, under the effect of the pressure generated by the gas generator; and
an injection nozzle for injecting the active ingredient which is arranged at the lower end of the reservoir, said device being characterized in that the tubular portion of the membrane has a generally funnel shape, said tubular portion having at least:
an upper segment having a generally frustoconical shape of a decreasing section along the direction of elongation of the membrane; and
a lower segment having a generally frustoconical shape of an increasing section along the direction of elongation of the membrane, the upper segment having an axial length greater than the axial length of the lower segment.

Such an asymmetrical funnel shape promotes the deployment of the membrane and its axial extension in the reservoir by limiting friction between the membrane and the inner face of the reservoir.

Indeed, on the upper segment of the membrane, the force exerted by the pressurized gas is applied perpendicularly to the surface of the membrane, so that the axial resultant of this force pushes the membrane downwards, along the direction of flow of the pressurized gas.

According to another feature, the membrane is sealed by a bottom that has the shape of a generally cylindrical disk which is axially delimited by a planar upper face in contact with the pressurized gas and a planar lower face.

The planar upper face of the bottom of the membrane provides a bearing surface on which the pressurized gas exerts an axially oriented force, in order to promote the elongation of the membrane.

In addition, the bottom of the membrane has a substantially curved shape which delimits a radial space with an inner wall of the reservoir.

The curved shape of the bottom of the membrane allows reducing friction between the bottom and the wall of the reservoir.

According to one form, the membrane is made of an elastomer-based material, so that the membrane is elastically deformable.

According to another feature, the membrane comprises a radial annular disk which is connected onto the tubular portion of the membrane, the annular disc axially bearing on an upper end of the reservoir.

According to another feature, the reservoir is sealed by an upper piston and a lower piston between which the liquid active ingredient is contained, said pistons being adapted to be axially pushed by the membrane under the effect of the pressure generated by the gas generator.

According to another feature, the active ingredient contained in the reservoir is selected from the group comprising the following active ingredients:

Methotrexate,
Adrenaline,
Sumatriptan,
Hydrocortisone,
Naloxone,
Midazolam,
Apomorphine,
Ethylnatrexone bromide,
Phytomenadione,
Chlorpromazine hydrochloride,
Zuclopenthixol acetate,
Danaparoid sodium,
Enoxaparin sodium,
Estradiol cypionate,
Medoxyprogesterone acetate,
Medroparin calcium,
Methylprednisolone acetate,
Heparin calcium, and
Terbulin.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
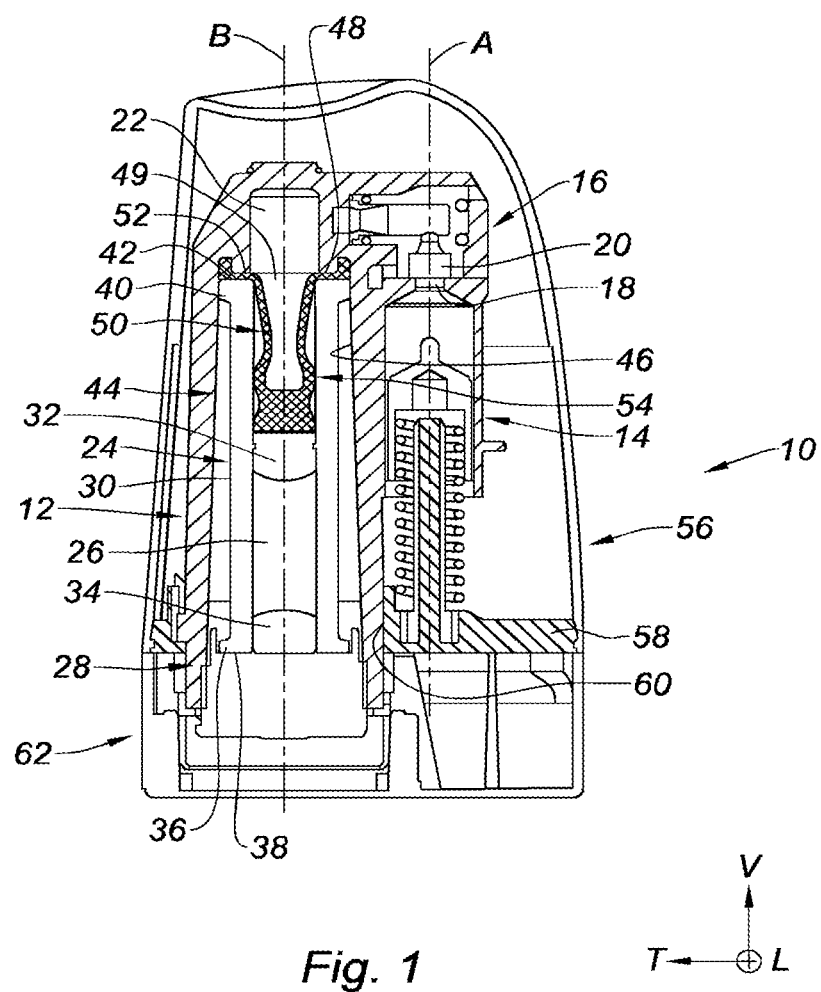
FIG. 1 is an axial sectional view which illustrates an injection device including a membrane in a rest position according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

In the present disclosure, in order to clarify the description and claims, the longitudinal, vertical and transverse terminology will be adopted in a non-limiting way with reference to the trihedron L, V, T indicated in the figures.

Furthermore, in the present application, the terms "upper," "lower," "horizontal," "vertical," and their derivatives refer to the position or the orientation of an element or a component, the position or orientation being considered with reference to the orientation of the device in the figures and to the trihedron L, V, T, without reference to Earth's gravity.

Similarly, the terms "axial" and "radial" should be understood with reference to the injection axis B of the injection device.

FIG. 1 shows a needleless injection device 10, or needleless syringe, which includes a U-shaped body 12 comprising successively a percussion device 14, a gas generator 16 comprising a primer 18 and a pyrotechnic charge 20, an expansion chamber 22, a reservoir 24 containing the liquid active ingredient 26 and an injection nozzle 28.

The percussion device 14 and the gas generator 16 constitute a first linear subassembly of the body 12 which extends axially along a vertical sliding axis A, and the reservoir 24 containing the active ingredient 26 and the injection nozzle 28 form a second linear subassembly of the body 12 which extends axially along a second vertical injection axis B.

These two subassemblies are connected to each other by the expansion chamber 22 which has an axis perpendicular to the axes A, B of the subassemblies.

The reservoir 24 is constituted by a glass tube 30 sealed by an upper piston 32 and a lower piston 34 between which the liquid active ingredient 26 is contained, the pistons being made of an elastically deformable elastomer-based material.

The reservoir 24 extends axially from a lower flange 36 which has an annular lower face 38 arranged facing the injection nozzle 28, to an upper flange 40 having an annular upper face 42.

The reservoir 24 is arranged in a housing 44 formed by the body 12, housing 44 which is delimited radially by a tubular wall 46 which extends about the injection axis B.

The housing 44 extends axially from an upper radial seat 48 which is formed by the body 12 and which delimits an outlet orifice 49 of the expansion chamber 22.

According to one form, the body 12 is made by plastic injection molding.

Figure 2:
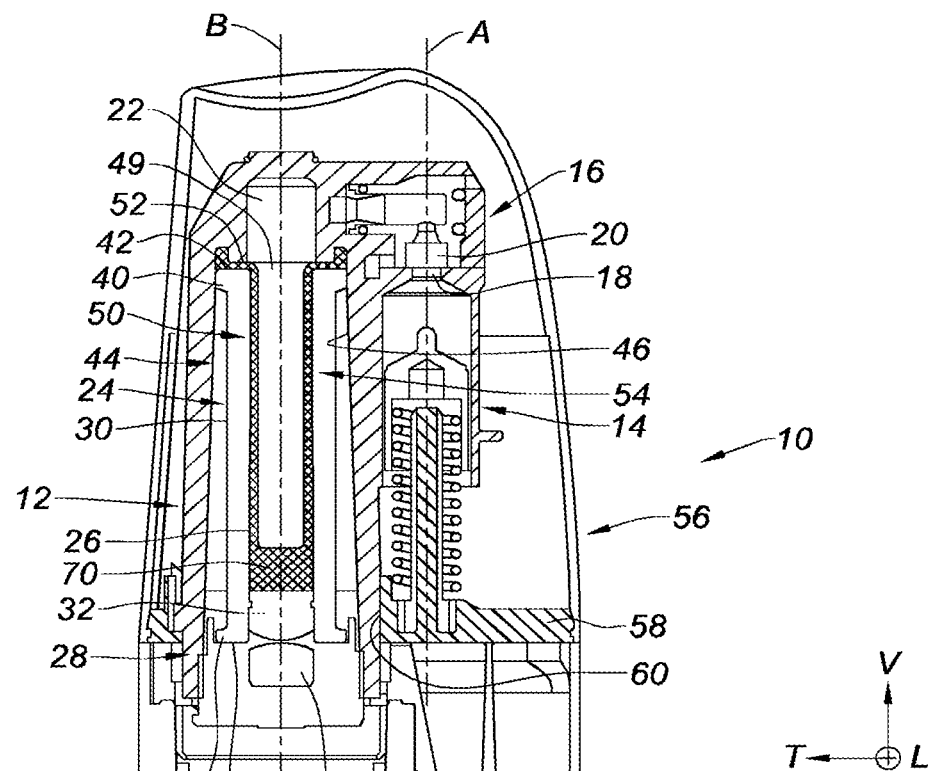
FIG. 2 is an axial sectional view which illustrates the injection device of FIG. 1 with the membrane in an extended position according to the present disclosure.

Also, according to FIGS. 1 and 2, the device 10 is equipped with a generally T-shaped elastically deformable membrane 50, which comprises a radial annular disc 52 which is interposed axially between the upper flange 40 of the reservoir 24 and the seat 48 formed by the body 12, and a tubular portion 54 which extends axially in the reservoir 24, from the annular disk 52.

As seen in FIG. 2, the tubular portion 54 of the membrane 50 is designed to extend axially, under the effect of the pressure of the gas generated by the gas generator 16, to push the upstream piston 32 downwards in order to eject the active ingredient 26 through the injection nozzle 28.

To this end, the membrane 50 is made of an elastomer-based material. More particularly, the membrane 50 is made of EPDM, that is to say, ethylene-propylene-diene monomer.

With reference to FIG. 1, the body 12 is wrapped by a hollow cover 56 which delimits a lower opening closed by a horizontal soleplate 58 forming a cover bottom.

The soleplate 58 delimits a circular passage 60 about the injection axis B which is adapted for the passage of the injection nozzle 28 and the lower end of the body 12, such that the nozzle 28 includes a lower segment protruding vertically downwards out of the cover 56.

More particularly, the nozzle 28 is screwed onto a free end emerging from the housing 44 formed by the body 12, the nozzle 28 compressing axially the assembly formed by the reservoir 24 and the membrane 50 on the seat 48 of the housing 44.

Also, the injection device 10 is equipped with a plug 62 which is removably mounted on the body 12 by a bayonet-type locking means.

Figure 3:
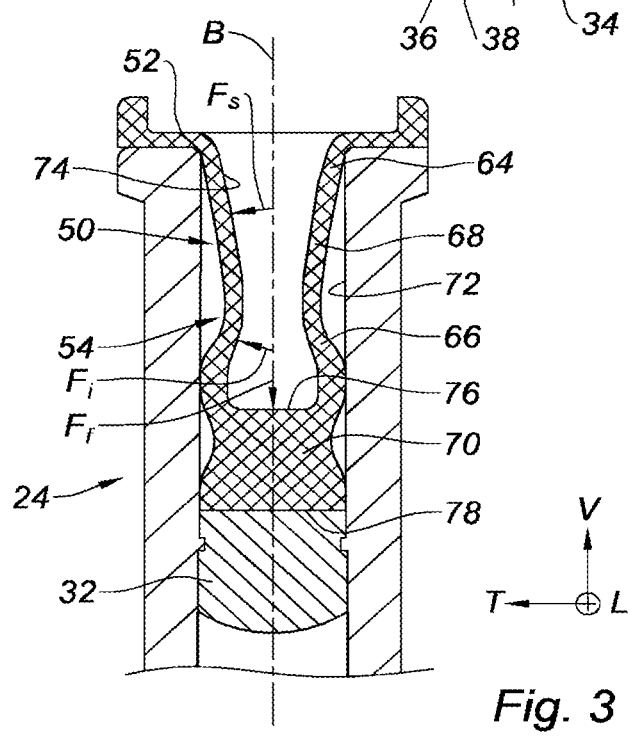
FIG. 3 is a detailed axial sectional view illustrating the membrane of FIG. 1 arranged in a reservoir according to the present disclosure.

In accordance with the present disclosure, the tubular portion 54 of the membrane 50 has a generally funnel shape, that is to say a curved shape, as seen in FIG. 3.

The tubular portion 54 has an upper segment 64, a lower segment 66, a connection portion 68 which connects the upper segment 64 and the lower segment 66, and a bottom 70.

"Upper segment" 64 means the upstream segment along the direction of flow of the gas in the injection device 10, and "lower segment" 66 means the downstream segment.

The upstream segment 64 has a generally frustoconical shape of a decreasing section along the direction of elongation of the membrane 50, that is to say a decreasing section from top to bottom.

Conversely, the lower segment 66 has a generally frustoconical shape of an increasing section along the direction of elongation of the membrane 50.

The connection portion 68 forms a radial narrowing of the membrane 50, so that the contact surface between the tubular portion 54 of the membrane 50 and the inner wall 72 of the reservoir 24 is limited, which reduces friction between the membrane 50 and the reservoir 24.

The upper segment 64 of the tubular portion 54 has an axial length greater than the axial length of the lower segment 66.

This feature allows promoting the axial elongation of the membrane 50 under the effect of the pressure generated by the gas generator 16.

Indeed, the force exerted by the pressurized gas on the membrane 50 is applied perpendicularly to the inner wall 74 of the Membrane 50.

As seen in FIG. 3, the force exerted on the upper segment 64 of the membrane 50 is illustrated by the arrow Fs, and the force exerted on the lower segment 66 of the membrane 50 is illustrated by the arrow Fi.

The force Fs has an axial resultant oriented downwards, which stretches the membrane 50 downwards, and the force Fi has an axial resultant oriented upwards, which opposes the axial resultant of the force Fs.

Since the upper segment 64 of the tubular portion 54 has an axial length greater than the axial length of the lower segment 66, the balance of the forces exerted on the membrane 50 by the pressurized gas tends to extend the tubular portion 54 of the membrane 50 downwards.

In addition, the force Ff which is exerted on the bottom 70 of the membrane 50 also tends to extend the tubular portion 54 of the membrane 50 downwards.

Also, it is observed that, along the direction of flow of the pressurized gas from top to bottom, or upstream to downstream, the pressure is exerted successively on the upper segment 64, and then on the lower segment 66 of the membrane 50, which also promotes the axial elongation of the membrane 50.

According to another aspect of the present disclosure, the bottom 70 of the membrane 50 is connected onto the lower segment 66 of the tubular portion 54 of the membrane 50.

The bottom 70 has the shape of a generally cylindrical disk which is axially delimited by an upper planar face 76 in contact with the pressurized gas and a lower planar face 78 axially bearing on the upper piston 32.

Also, the bottom 70 of the membrane 50 has a substantially curved shape which delimits a radial space with the inner wall 72 of the reservoir 24, in order to limit friction between the membrane 50 and the reservoir 24.

As used herein, the phrase "at least one of A, B, and C" should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A needleless injection device including:
   a body forming a housing;
   a gas generator;
   a tubular reservoir that contains an active ingredient to be injected, the tubular reservoir extending axially in the housing and having an upper end and a lower end;
   a T-shaped elastically deformable membrane comprising a tubular portion that is configured to deformably extend and lie axially in the tubular reservoir under an effect of a pressurized gas generated by the gas generator and a bottom having a substantially curved shape delimiting a radial space with an inner wall of the reservoir; and
   an injection nozzle for injecting the active ingredient which is arranged at the lower end of the tubular reservoir,
   wherein the tubular portion of the membrane is funnel shaped and includes at least:
      an upper segment having a curved frustoconical shape of a decreasing section along a direction of axial elongation of the membrane in an undeformed state, the curved frustoconical shape of the upper segment defining a first curve in the direction of axial elongation; and
      a lower segment having a curved frustoconical shape of an increasing section along the direction of axial elongation of the membrane in the undeformed state, the curved frustoconical shape of the lower segment defining a second curve in the direction of axial elongation contiguous with the first curve of the upper segment,
   wherein an axial length of the first curve is greater than an axial length of the second curve;
   wherein the bottom includes upper and lower portions that contact the inner wall and extend along a diameter of the housing, and an intermediate portion between the upper and lower portions, the radial space delimited between the inner wall of the reservoir and the intermediate portion.

2. The needleless injection device according to claim 1, wherein the membrane is sealed by the bottom having a cylindrical disk shape that is axially delimited by a planar upper face in contact with the pressurized gas and a planar lower face.

3. The needleless injection device according to claim 1, wherein the membrane is made of an elastomer-based material.

4. The needleless injection device according to claim 1, wherein the membrane comprises a radial annular disk that is connected on the tubular portion of the membrane, the radial annular disc axially bearing on an upper end of the tubular reservoir.

5. The needleless injection device according to claim 1, wherein the tubular reservoir is sealed by an upper piston and a lower piston between which the active ingredient is contained, said pistons adapted to be axially pushed by the membrane under the effect of the pressure generated by the gas generator.

6. The needleless injection device according to claim 1, wherein the active ingredient contained in the reservoir is selected from the group consisting of Methotrexate, Adrenaline, Sumatriptan, Hydrocortisone, Naloxone, Midazolam, Apomorphine, Ethylnatrexone bromide, Phytomenadione, Chlorpromazine hydrochloride, Zuclopenthixol acetate, Danaparoid sodium, Enoxaparin sodium, Estradiol cypionate, Medoxyprogesterone acetate, Medroparin calcium, Methylprednisolone acetate, Heparin calcium, and Terbulin.

7. A needleless injection device including:
a body forming a housing;
a gas generator;
a tubular reservoir that contains an active ingredient to be injected, the tubular reservoir extending axially in the housing and having an upper end and a lower end;
a T-shaped elastically deformable membrane comprising a tubular portion that is configured to deformably extend and lie axially in the tubular reservoir under an effect of a pressure generated by the gas generator and a bottom having a substantially curved shape delimiting a radial space with an inner wall of the reservoir; and
an injection nozzle for injecting the active ingredient which is arranged at the lower end of the tubular reservoir,
wherein the tubular portion of the membrane is funnel shaped and includes at least:
an upper segment having a curved frustoconical shape of a decreasing section along a direction of axial elongation of the membrane in an undeformed state, the curved frustoconical shape of the upper segment defining a first curve in the direction of axial elongation; and
a lower segment having a curved frustoconical shape of an increasing section along the direction of axial elongation of the membrane in the undeformed state, the curved frustoconical shape of the lower segment defining a second curve in the direction of axial elongation contiguous with the first curve of the upper segment,
wherein an axial length of the first curve is greater than an axial length of the second curve;
wherein the membrane is made of an ethylene-propylene-diene monomer;
wherein the bottom includes upper and lower portions that contact the inner wall and extend along a diameter of the housing, and an intermediate portion between the upper and lower portions, the radial space delimited between the inner wall of the reservoir and the intermediate portion.

8. A needleless injection device including:
a body forming a housing;
a gas generator;
a tubular reservoir that contains an active ingredient to be injected, the tubular reservoir extending axially in the housing and having an upper end and a lower end;
a T-shaped elastically deformable membrane comprising a tubular portion that is configured to deformably extend and lie axially in the tubular reservoir under an effect of a pressure generated by the gas generator and a bottom having a substantially curved shape delimiting a radial space with an inner wall of the reservoir; and
an injection nozzle for injecting the active ingredient which is arranged at the lower end of the tubular reservoir,
wherein the tubular portion of the membrane is a generally curved funnel shape and includes at least:
an upper segment having a curved frustoconical shape of a decreasing section along a direction of axial elongation of the membrane in an undeformed state, the curved frustoconical shape of the upper segment defining a first curve in the direction of axial elongation; and
a lower segment having a curved frustoconical shape of an increasing section along the direction of axial elongation of the membrane in the undeformed state, the curved frustoconical shape of the lower segment defining a second curve in the direction of axial elongation contiguous with the first curve of the upper segment,
wherein an axial length of the first curve is greater than an axial length of the second curve;
wherein the bottom includes upper and lower portions that contact the inner wall and extend along a diameter of the housing, and an intermediate portion between the upper and lower portions, the radial space delimited between the inner wall of the reservoir and the intermediate portion.

* * * * *